United States Patent [19]

Georgiev et al.

[11] Patent Number: 4,777,262
[45] Date of Patent: Oct. 11, 1988

[54] 5-(SUBSTITUTED THIOMETHYL)-3-PHENYL-3-(1H-IMIDAZOL-1-YLMETHYL)-2-METHYLISOXAZOLIDINE DERIVATIVES

[75] Inventors: Vassil S. Georgiev, Penfield; George B. Mullen, Avon, both of N.Y.

[73] Assignee: Pennwalt Corporation, Philadelphia, Pa.

[21] Appl. No.: 104,626

[22] Filed: Oct. 2, 1987

[51] Int. Cl.$^4$ ................ A01N 43/52; C07D 233/60
[52] U.S. Cl. ...................................... 548/240; 548/341
[58] Field of Search ........................................ 548/240

[56] References Cited

U.S. PATENT DOCUMENTS

| 3,709,901 | 1/1973 | Draber et al. | 548/235 |
| 3,711,495 | 1/1973 | Kulsa et al. | 548/240 |
| 3,915,978 | 10/1975 | Kulsa et al. | 548/240 |
| 3,987,179 | 10/1975 | Nadelson | 514/378 |
| 4,010,176 | 3/1977 | Kulsa et al. | 548/242 |
| 4,510,154 | 4/1985 | Yoshida et al. | 514/365 |
| 4,719,306 | 1/1988 | Georgiev | 548/240 |
| 4,723,021 | 2/1988 | Georgiev | 548/240 |

FOREIGN PATENT DOCUMENTS

| 171137 | 2/1986 | European Pat. Off. | 548/215 |
| 54-76579 | 6/1979 | Japan . | |

OTHER PUBLICATIONS

Kelly, R. C. et al., Chemical Abstract 93:114498u (1980), Abstracting German Offen. 2,918,878 (Nov. 22, 1979).
Haken, P. T. et al., Chemical Abstract 93:132471j (1980), Abstracting Brit. Pat. Appln. 2,024,218 (Jan. 9, 1980).
Sokolov, S. V. et al., Chemical Abstract 55:7399 (1961) Abstracting "Isoxazole Compounds III. Synthesis of Some Isoxazolylazoles", Zhur, Obshchei Khim, 30, pp. 1781–1787 (1960).
Kano, H., et al., Chem. Abstract 62:9139a (1965), Abstracting French No. 1,376,432 (Oct. 23, 1964).
Kano, H. et al., Chemical Abstract 63:8367a (1965), Abstracting French 1,380,177 (Nov. 27, 1964).
Takahi, Y. et al., Chemical Abstract 81:22233c (1974), Abstracting Japan Kokai 7399,336 (Dec. 15, 1973).
Boyce, C. B. et al., Chemical Abstract 87:23258a (1977), Abstracting German Offen. 2,639,189 (Mar. 10, 1977).
Funaki, Y. et al., Chemical Abstract 92:128915u (1980), Abstracting Japan Kokai 79 76,579 (Jun. 19, 1979).

Primary Examiner—Donald G. Daus
Assistant Examiner—Mark W. Noel

[57] ABSTRACT 5-(Substituted thiomethyl)-3-phenyl-3-(1H-imidazol-1-ylmethyl)-2-methylisoxazolidine derivatives are useful as antifungal agents.

5 Claims, No Drawings

5-(SUBSTITUTED THIOMETHYL)-3-PHENYL-3-(1H-IMIDAZOL-1-YLMETHYL)-2-METHYLISOXAZOLIDINE DERIVATIVES

BACKGROUND OF THE INVENTION

This invention relates generally to substituted 2-methylisoxazolidines and more specifically to 5-(substituted thiomethyl)-3-phenyl-3-(1H-imidazol-1-ylmethyl)-2-methylisoxazolidine derivatives which are useful as antifungal agents.

BRIEF SUMMARY OF THE INVENTION

In accordance with this invention there are provided compounds of the formula:

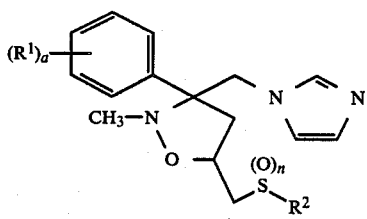

and the pharmaceutically acceptable acid addition salts thereof, in the form of their enantiomers or mixtures of their enantiomers including diastereomeric pairs of such enantiomers, wherein;
a = 1 or 2,
$R^1$ is selected from hydrogen, halogen, lower alkyl, lower alkoxy and combinations thereof, provided that the ortho position is hydrogen,
$R^2$ is selected from lower alkyl, benzyl and (substituted phenyl)methyl groups, wherein the substituents on the phenyl rings are selected from one or more halogens, lower alkyl, and lower alkoxy groups and combinations thereof, and
n = 0 to 2.

DETAILED DESCRIPTION OF THE INVENTION

The compounds of this invention are useful as antifungal agents. They have in vitro activity against yeast and systemic mycoses and dermatophytes as determined by broth and agar testing techniques [McGinnis, M. R., *Laboratory Handbook of Medical Mycology*, Academic Press, New York, N.Y. (1980)]. The compound prepared in Example 1 was found to have good to moderate inhibitory activity against a broad spectrum of organisms including Trichophyton mentagrophytes, Trichophyton rubrum, Trichophyton tonsurans, Epidermophyton floccosum and Candida stellatoidea with a minimum inhibitory concentration, MIC, of 0.7 to 70 μg/ml.

Because of their antifungal activity, the compounds of this invention can be used, for example, in suitable liquid, semisolid or solid carriers in the form of solutions, emulsions, suspensions, dispersions, ointments, aerosols, soaps, detergents, and powders in amounts effective to combat systemic and dermatophylic fungal infections in warm-blooded animals (1 to 20 percent active ingredient).

The compounds of this invention are those of the formula:

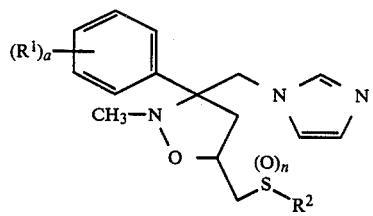

and the pharmaceutically acceptable acid addition salts thereof, in the form of their enantiomers or mixtures of their enantiomers including diastereomeric pairs of such enantiomers, wherein;
a = 1 or 2,
$R^1$ is selected from hydrogen, halogen, lower alkyl, lower alkoxy and combinations thereof, provided that the ortho position as hydrogen,
$R^2$ is selected from lower alkyl, benzyl and (substituted phenyl)methyl groups, wherein the phenyl rings can be substituted with one or more halogens, lower alkyl and lower alkoxy groups and combinations thereof. The sulfur atom may be oxidized to provide the corresponding sulfoxide and sulfone analogs (n = 1 or 2, respectively).

By halogen is meant chlorine, bromine, fluorine and iodine with chlorine and fluorine being preferred. By lower alkyl is meant alkyl groups containing one to four (1-4) carbons and by lower alkoxy is meant alkyl groups containing one to six (1-6) carbons. Such groups with three or more carbons can have a branched or unbranched chain.

The 5-(substituted thiomethyl)-3-phenyl-3-(1H-imidazol-1-ylmethyl)-2-methylisoxazolidine derivatives of the invention are obtained as a mixture of cis- and trans-diastereomers due to the presence of two asymmetric carbon atoms in the isoxazolidine ring. The diastereomeric mixture is conveniently separated by flash chromatography on silica gel using halogenated hydrocarbons (preferably dichloromethane and chloroform), alkanols (preferably methanol and ethanol), ethyl acetate and such, as eluents. The eluents may be used alone or in combinations, such as the ones comprised of 95-99% halogenated hydrocarbon and 1-5% alkanol by volume. The stereochemistry of the two asymmetric carbons atoms in the isoxazolidine ring may be determined by conventional methods that include X-ray crystallography, nuclear magnetic resonance spectroscopy, circular dichroism and optical rotatory dispersion. Both the cis- and trans-diastereoisomers are resolvable into their optical enantiomers with (+)- and (−)-optical rotations by standard techniques such as fractional recrystallization of the diastereomeric salts with optically active organic acids such as (+)- and (−)-tartaric acid, (+)- and (−)-dibenzoyltartaric acid and the like.

The compounds of this invention can be prepared as illustrated in the following diagram. The synthesis of the nitrone precursors 1 is accomplished by reacting an appropriately substituted 2-imidazolylacetophenone (prepared from a brominated acetophenone and imidazole) with N-methylhydroxylamine hydrochloride as described in our copending application Ser. No. 900,856 filed Aug. 27, 1986 whose disclosure is incorporated herein by reference. Subsequent reaction of the nitrone with an appropriate allyl sulfide derivative 2 provides a diastereomeric mixture of the desired cis- and trans-5-

(substituted thiomethyl)-3-phenyl-3-(1H-imidazol-1-ylmethyl)-2-methylisoxazolidine 3.

The allyl sulfides 2 can be prepared by reaction of the corresponding alkyl mercaptans with sodium hydride and allyl bromide in ether. Allyl sulfides 2 [$R^2$=CH$_3$, CH(CH$_3$)$_2$] are commercially available.

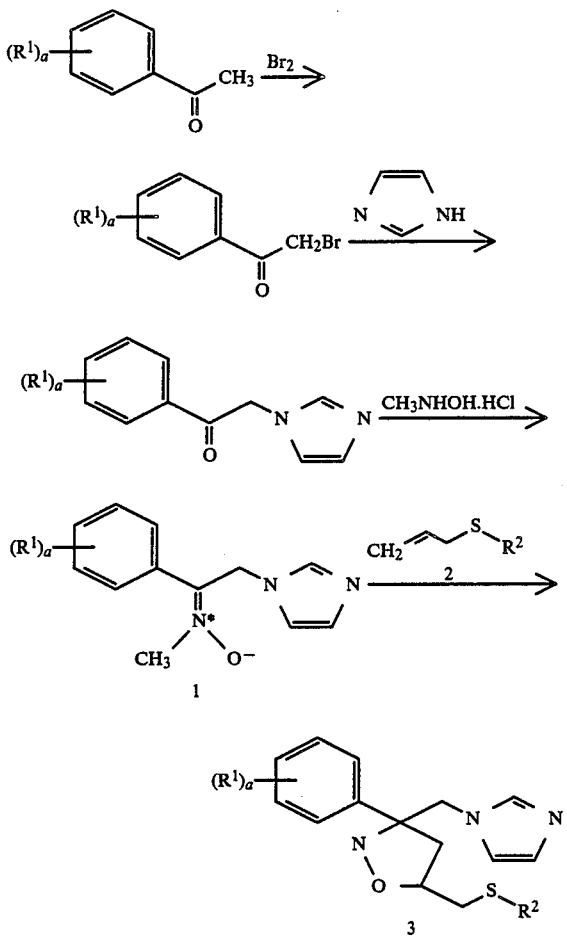

The compounds of the invention are all basic and thus can form salts with pharmaceutically acceptable inorganic and organic acids such as, for example, acetic acid, maleic acid, malic acid, fumaric acid, succinic acid, succinamic acid, tartaric acid, citric acid, lactic acid, hydrochloric acid, hydrobromic acid, hydroiodic acid, nitric acid, sulfuric acid and phosphoric acid.

The preparation of the compounds of this invention is further illustrated by the following examples.

EXAMPLE 1

3-(4-Chlorophenyl)-3-(1H-imidazol-1-ylmethyl)-2-methyl-5-[(methylthio)methyl]isoxazolidine (3, $R^1$=4-Cl, $R^2$=CH$_3$)

A solution of 16.50 g (0.0661 mol) of 1-(4-chlorophenyl)-2-(1-imidazol-1-yl)-N-methylethanimine N-oxide (1, $R^1$=4-Cl) [prepared by reacting 2-(1H-imidazol-1-yl)-4'-chloroacetophenone (22.05 g, 0.10 mol), N-methylhydroxylamine hydrochloride (10.65 g, 0.127 mol) and sodium bicarbonate (10.84 g, 0.129 mol) in 300 ml ethanol] and 15.0 ml (0.137 mol) of allyl methyl sulfide (2, $R^2$=CH$_3$) in 150 ml of toluene was heated to reflux under a nitrogen atmosphere and stirred for 30 hours, then cooled to ambient temperature and concentrated in vacuo. The residual dark oil, containing a cis- and trans-diastereomeric mixture of compound 3 ($R^1$=4-Cl, $R^2$=CH$_3$) was flash chromatographed on neutral silica gel using a 98:2 by volume mixture of chloroform and methanol as eluent.

Isomer A (4.53 g, 20%) has a melting point of 142°–144° C. (ethyl acetate). Anal. Calcd. for $C_{16}H_{20}ClN_3OS$: C, 56.88; H, 5.97; Cl, 10.49; N, 12.44; S, 9.49. Found: C, 56.95; H, 6.01; Cl, 10.21; N, 12.39; S, 9.63.

EXAMPLE 2

3-(1H-Imidazol-1-ylmethyl)-2-methyl-5-{[(1-methylethyl)thio]methyl}-3-phenylisoxazolidine [3, $R^1$=H, $R^2$=CH(CH$_3$)$_2$]

Compound 3 [$R^1$=H, $R^2$=CH(CH$_3$)$_2$] was prepared by a method similar to that described in Example 1 from 5.19 g (0.0241 mol) of 2-(1H-imidazol-1-yl)-N-methyl-1-phenylethanimine N-oxide (1, $R^1$=H) and 2.80 g (0.0241 mol) of allyl isopropyl sulfide [2, $R^2$=CH(CH$_3$)$_2$]. The resulting cis- and trans-diastereomeric mixture of compound 3 [$R^1$=H, $R^2$=CH(CH$_3$)$_2$] was flash chromatographed on neutral silica gel using a 99:1 by volume mixture of chloroform and methanol as eluent.

Isomer A (2.48 g, 31%) has a melting point of 57.5°–59° C. (ether:cyclohexane, 1:2). Anal. Calcd. for $C_{18}H_{25}N_3OS$·HCl: C, 58.76; H, 7.12; Cl, 9.64; N, 11.42; S, 8.71. Found: C, 58.48; H, 7.12; Cl, 9.88; N, 11.38; S, 8.90.

EXAMPLE 3

5-{[[(3,4-Dichlorophenyl)methyl]thio]methyl}-3-(1H-imidazol-1-ylmethyl)-2-methyl-3-phenylisoxazolidine (3; $R^1$=H, $R^2$=CH$_2$C$_6$H$_3$Cl$_2$-3,4)

Compound 3 ($R^1$=H, $R^2$=CH$_2$C$_6$H$_3$Cl$_2$-3,4) was prepared by a method similar to that described in Example 1 from 5.00 g (0.023 mol) of 2-(1H-imidazol-1-yl)-N-methyl-1-phenylethanimine N-oxide (1, $R^1$=H) and 8.04 g (0.0345 mol) of allyl(3,4-dichlorophenyl)methyl sulfide (2, $R^2$=CH$_2$C$_6$H$_3$Cl$_2$-3,4). The resulting cis- and trans-diastereomeric mixture of compound 3 ($R^1$=H, $R^2$=CH$_2$C$_6$H$_3$Cl$_2$-3,4) was flash chromatographed on neutral silica gel using a 99:1 by volume mixture of chloroform and methanol as eluent. Isomer A (0.93 g, 9%) has a melting point of 105.5°–108° C. (ethyl acetate). Anal. Calcd. for $C_{22}H_{23}Cl_2N_3OS$: C, 58.93; H, 5.17; Cl, 15.81; N, 9.37; S, 7.15. Found: C, 58.66; H, 5.00; Cl, 15.96; N, 9.26; S, 7.23.

EXAMPLE 4

5-{[[(4-Chlorophenyl)methyl]thio]methyl}-3-(1H-imidazol-1-ylmethyl)-2-methyl-3-phenylisoxazolidine (3, $R^1$=H, $R^2$=CH$_2$C$_6$H$_4$Cl-4)

Compound 3 ($R^1$=H, $R^2$=CH$_2$C$_6$H$_4$Cl-4) was prepared by a method similar to that described in Example 1 from 4.60 g (0.021 mol) of 2-(1H-imidazol-1-yl)-N-methyl-1-phenylethanimine N-oxide (1, $R^1$=H) and 5.0 g (0.023 mol) of allyl(4-chlorophenyl)methyl sulfide (2, $R^2$=CH$_2$C$_6$H$_4$Cl-4). The resulting cis- and trans-diastereomeric mixture of compound 3($R^1$=H, $R^2$=CH$_2$C$_6$H$_4$Cl-4) was flash-chromatographed on neutral silica gel using a 99:1 by volume mixture of chloroform and methanol as eluent.

Isomer A·HCl (1.31 g, 13.6%) has a melting point of 181°–185° C. (ether). Anal. Calcd. for $C_{22}H_{25}Cl_2N_3OS$:

C, 58.66; H, 5.59; Cl, 15.74; N, 9.33; S, 7.12. Found: C, 58.10; H, 5.62; Cl, 15.72; N, 9.20; S, 7.38.

EXAMPLE 5

5-[[[(Substituted phenyl)methyl]thio]methyl]-3-(1H-imidazol-1-ylmethyl)-2-methyl-3-(substituted phenyl)isoxazolidines By following essentially the same method as Example 4 and substituting allyl[(4-methylphenyl)methyl]sulfide or allyl(4-methoxyphenyl)methyl sulfide for allyl(4-chlorophenyl)methyl sulfide and substituting for 2-(1H-imidazol-1-yl)-N-methyl-1-phenylethanimine N-oxide one of the following compounds:

1-(4-methoxphenyl)-2-(1H-imidazol-1-yl)-N-methylethanimine N-oxide, 1-(4-methylphenyl)-2-(1H-imidazol-1-yl)-N-methylethanimine N-oxide, 1-(4-chloro-3-methylphenyl)-2-(1H-imidazol-1-yl)-N-methylethanimine N-oxide, 1-(3,4-dichlorophenyl)-2-(1H-imidazol-1-yl)-N-methylethanimine oxide, 1-(3-methylphenyl)-2-(1H-imidazol-1-yl)-N-methylethanimine N-oxide, or 1-(3-methoxyphenyl)-2-(1H-imidazol-1-yl)-N-methylethanimine N-oxide, the corresponding 5-[[[(substituted phenyl)methyl]thio]methyl]-3-(1H-imidazol-1-yl)-2-methyl-3-(substituted phenyl)isoxazolidines are prepared.

Salts of the compounds of the invention can be prepared as known in the art, for example, by dissolving the compound in a 10:1 by volume mixture of ethanol and aqueous acid such as HCl (in Examples 2 and 4) or HNO$_3$, evaporating the solvent, and then recrystallizing the crude salt, for example, from methanol-ether, 1:3 by volume in the case of HCl salts, and ethanol in the case of HNO$_3$ salts.

The sulfoxide derivatives are prepared by dissolving the thio derivatives in methylene chloride at low temperatures (dry ice-acetone bath) of about $-80°$ C., adding 85% m-chloroperbenzoic acid, allowing the solution to gradually warm to room temperature, washing the resulting solution with sodium bicarbonate, drying the solution over anhydrous magnesium sulfate and then evaporating the methylene chloride to provide the crude product which is flash chromatographed to provide pure isomers.

The sulfones are prepared by dissolving the thio derivatives in methylene chloride at ambient temperature, adding 2.2 equiv. of 85% m-chloroperbenzoic acid, washing the resulting solution with sodium bicarbonate, drying the solution over anhydrous magnesium sulfate and then evaporating the methylene chloride to provide the crude product which is flash chromatographed to provide pure isomers.

We claim:

1. A compound of the formula:

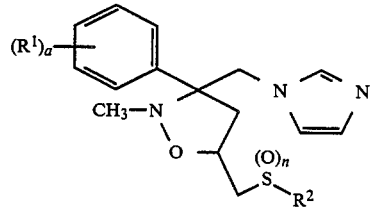

and the pharmaceutically acceptable acid addition salts thereof, in the form of their enantiomers or mixtures of their enantiomers including diastereomeric pairs of such enantiomers, wherein a=1 or 2, $R^1$ is selected from hydrogen, halogen, lower alkyl, lower alkoxy and combinations thereof, provided that the ortho position is hydrogen, $R^2$ is selected from lower alkyl, benzyl and (substituted phenyl)methyl groups, wherein the substituents on the phenyl rings are selected from one to three halogens, lower alkyl, and lower alkoxy groups and combinations thereof and n=0 to 2.

2. The compound of claim 1 wherein the compound is 3-(4-chlorophenyl)-3-(1H-imidazol-1-ylmethyl)-2-methyl-5-[(methylthio)methyl]isoxazolidine.

3. The compound of claim 1 wherein the compound is 3-(1H-imidazol-1-ylmethyl)-2-methyl-5-{[(1-methylethyl)-thio]methyl}-3-phenylisoxazolidine.

4. The compound of claim 1 wherein the compound is 5-{[[(3,4-dichlorophenyl)methyl]thio]methyl}-3-(1H-imidazol-1-ylmethyl)-2-methyl-3-phenylisoxazolidine.

5. The compound of claim 1 wherein the compound is 5-{[[(4-chlorophenyl)methyl]thio]methyl}-3-(1H-imidazol-1-ylmethyl)-2-methyl-3-phenylisoxazolidine.

* * * * *